United States Patent
McGlone

(10) Patent No.: US 11,007,202 B2
(45) Date of Patent: *May 18, 2021

(54) PHEROMONE COMPOSITIONS FOR STIMULATING EARLY ONSET OF ESTRUS AND REDUCING LABOR NEEDS IN BREEDING PERI-PUBERTAL SUIDS AND METHODS OF USE

(71) Applicant: Texas Tech University System, Lubbock, TX (US)

(72) Inventor: John J. McGlone, Lubbock, TX (US)

(73) Assignee: TEXAS TECH UNIVERSITY SYSTEM, Lubbock, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/217,752

(22) Filed: Dec. 12, 2018

(65) Prior Publication Data

US 2019/0183905 A1      Jun. 20, 2019

Related U.S. Application Data

(60) Provisional application No. 62/598,310, filed on Dec. 13, 2017.

(51) Int. Cl.
| | | |
|---|---|---|
| *A61K 31/5685* | (2006.01) | |
| *A61K 31/568* | (2006.01) | |
| *A61K 31/47* | (2006.01) | |
| *A61P 15/08* | (2006.01) | |
| *A61K 47/44* | (2017.01) | |
| *A61K 9/00* | (2006.01) | |
| *A61K 9/12* | (2006.01) | |
| *A61K 47/10* | (2017.01) | |
| *A61K 47/24* | (2006.01) | |
| *A61K 47/06* | (2006.01) | |
| *A61K 47/08* | (2006.01) | |
| *A61K 47/20* | (2006.01) | |

(52) U.S. Cl.
CPC .......... *A61K 31/5685* (2013.01); *A61K 9/007* (2013.01); *A61K 9/008* (2013.01); *A61K 9/0043* (2013.01); *A61K 9/122* (2013.01); *A61K 9/124* (2013.01); *A61K 31/47* (2013.01); *A61K 31/568* (2013.01); *A61K 47/06* (2013.01); *A61K 47/08* (2013.01); *A61K 47/10* (2013.01); *A61K 47/20* (2013.01); *A61K 47/24* (2013.01); *A61K 47/44* (2013.01); *A61P 15/08* (2018.01)

(58) Field of Classification Search
CPC .... A61K 31/5685; A61K 9/007; A61K 47/24; A61K 9/124; A61K 47/06; A61K 9/008; A61K 47/08; A61K 47/20; A61K 31/568; A61K 31/47; A61K 47/44; A61K 9/0043; A61K 9/122; A61K 47/10; A61K 2300/00; A61P 15/08
See application file for complete search history.

(56) References Cited

U.S. PATENT DOCUMENTS

| | | | |
|---|---|---|---|
| 9,352,011 B2 | 5/2016 | Webel et al. | |
| 2006/0252738 A1 | 11/2006 | Avelino et al. | |

FOREIGN PATENT DOCUMENTS

| | | |
|---|---|---|
| RU | 171378 U1 | 5/2017 |
| WO | 2017087468 A1 | 5/2017 |

OTHER PUBLICATIONS

International Search Report and Written Opinion received for PCT App. No. PCT/US2018/065171; dated Mar. 5, 2019; 8 pages.

*Primary Examiner* — Snigdha Maewall
(74) *Attorney, Agent, or Firm* — Polsinelli P.C.

(57) ABSTRACT

The present disclosure provides for pheromonal compositions and methods of using the compositions for stimulating early onset of estrus in a peri-pubertal suid and methods of improving performance of the peri-pubertal female suid. The composition may comprise at least one steroid hormone and a heterocyclic aromatic compound. The method comprises administering the pheromone composition to the suid for a period of time.

28 Claims, 13 Drawing Sheets

PHEROMONE COMPOSITIONS FOR STIMULATING EARLY ONSET OF ESTRUS AND REDUCING LABOR NEEDS IN BREEDING PERI-PUBERTAL SUIDS AND METHODS OF USE

FIELD OF THE INVENTION

The present invention relates to compositions comprising a combination of pheromonal agents and methods of using such compositions to modify behavior in an animal. More particularly, the present disclosure is concerned with a pheromone composition comprising a combination of a heterocyclic aromatic compound and at least one androgen steroid, and the use of such composition to stimulate early onset of estrus in a peri-pubertal pig, and reduce the labor needs associated with breeding young female suids.

BACKGROUND

The biology of swine growth and development imposes constraints on herd management, facilities design, and productivity. The boundaries of some biological parameters are relatively inflexible, but for others, the boundaries are highly influenced by genetics or the environment. Age at puberty is one of the flexible parameters. The time at which first estrus occurs in females is usually at 6-8 months of age, but depends on breed, environment and season of the year. Further, timing of first estrus in peri-pubertal gilts can also depend on exposure to male odors, usually provided in the form of a live, adult boar. For instance, if peri-pubertal pigs are kept in a conventional finishing barn without exposure to adult male pigs and their odor, peri-pubertal females may not have their first fertile estrus for many months (8 months of age or later).

As the aim of efficient pig production is to maximize growth and turnaround of animals, accelerating the onset of puberty in peri-pubertal gilts would significantly improve productivity. However, using the current methods of the industry to induce estrus (exposing peri-pubertal suids to boars) and then identifying first estrus is time consuming and labor intensive. For instance, peri-pubertal pig may have to be exposed to a boar multiple times to successfully induce estrus. Further, handling animals during this phase of pig farming can even be dangerous to the humans that work with them.

Pheromone signals are known to play a major role in mammalian reproduction and behavior. Scientific literature points to salivary steroid molecules androstenone and androstenol as the recognized boar pheromone that is responsible for inducing reproduction in the female pig (see Melrose et al., "Androgen steroids associated with boar odour as an aid to the detection of oestrous in pig artificial insemination", The British Veterinary Journal, 127, 497-502 (1971); see also Perry et al., "Pig courtship behaviour: pheromonal property of androstene steroids in male submaxillary secretion", Animal Production, 31, 191-199 (1980)). Products such as Boarmate™ (ITSI, Canada), which contain androstenone as the sole active, have long been sold on the market to detect female pigs in heat and have been used to save time and money when breeding pigs. Further, compositions for the inducement of reproductive behavior in adult female suids have been described (U.S. Pat. No. 9,480,689). However, there are currently no known methods that may be used to accelerate the onset of puberty in peri-pubertal gilts.

Accordingly, to increase productivity in pig farming, there is a need within the industry for methods of stimulating early onset of estrus, reducing labor, and improving human safety when peri-pubertal gilts are managed.

SUMMARY OF THE PRESENT INVENTION

One aspect of the present disclosure encompasses a method of stimulating early onset of estrus in a peri-pubertal suid. The method comprises administering a pheromone composition to the suid, which composition comprises a combination of pheromonal agents. The pheromonal agents comprise at least one steroid hormone and one heterocyclic aromatic compound. The pheromone composition may be administered for a period of time ranging from about 25 to about 35 days.

The steroid hormone may be an androgen steroid selected from the group consisting of androstenone, androstenol, androstadienone, estratetraenol, and combinations thereof. The androgen steroid may be present in an amount from between about 0.0001% to about 1% (w/w) of the composition.

The androgen steroid may consist of androstenone and androstenol. When the androgen steroid may consist of androstenone and androstanol, the androstenone is present in the composition at a concentration ranging from between about 0.0003% to about 0.0005% (w/w), and the androstenol is present in the composition at a concentration ranging from between about 0.0003% to about 0.0005% (w/w).

Alternatively, when the androgen steroid may consist of androstenone and androstanol, the androstenone is present in the composition at a concentration ranging from between about 0.001% to about 0.003% (w/w), and the androstenol is present in the composition at a concentration ranging from between about 0.001% to about 0.003% (w/w).

The heterocyclic aromatic compound may be quinolone. When the heterocyclic aromatic compound is quinolone, the compound is present in an amount from between about 0.0007% to about 0.0009% (w/w) of the composition.

The composition may further comprise a carrier solvent. The carrier solvent may be selected from the group consisting of lipophilic organic diluents, alcohols, ethylene glycol, propylene glycol, dipropylene glycol, ether, chloroform, benzene, carbon disulfide, oils including non-volatile and volatile liquids and oils, water, and combinations thereof. The alcohol may be selected from the group consisting of ethanol, propanol, isopropanol, butanol, pentanol, hexanol, heptanol, octanol, phenyl ethyl alcohol, and combinations thereof. The composition may further comprise an additional component selected from the group consisting of a surfactant, a thickener, a foaming agent, a lubricant, a propellant, a fragrance, and combinations thereof.

The composition may be formulated as a spray composition. The spray composition may comprise about 0.0003% to about 0.0005% (w/w) androstenone, about 0.0003% to about 0.0005% (w/w) androstenol (w/w), about 0.0003% to about 0.0005% (w/w) quinolone, about 3% to about 7% (w/w) isopropanol, and about 89% to about 93% (w/w) water. Alternatively, the spray composition may comprise about 0.001% to about 0.003% (w/w) androstenone, about 0.001% to about 0.003% (w/w) androstenol, about 0.001% to about 0.003% (w/w) quinolone, about 3% to about 7% (w/w) isopropanol, and about 89% to about 93% (w/w) water.

The composition may be formulated as a foaming composition. The spray composition may comprise about 0.001% to about 0.003% (w/w) androstenone, about 0.001% to about 0.003% (w/w) androstenol, about 0.001% to about 0.003% (w/w) quinolone, about 1% to about 10% (w/w) glycerin lubricant, about 70% to about 95% (w/w) water, and about 5% to about 20% (w/w) propellent.

The composition may be administered to the olfactory system of the suid, and administering the pheromone composition comprises spraying the suid with the composition, placing the composition in the environment of the suid, or spraying the suid's environment with the composition. Administering the pheromone composition may comprise placing the composition in the environment of the suid. Placing the composition in the environment of the suid may comprise applying the composition to a rope in the environment of the suid. The pheromone composition may be administered for a duration of time ranging from about 10 to about 50 days. The method of claim 21, wherein administering the pheromone composition comprises placing the composition in the environment of the suid at a rate of about 3 to about 5 ml daily for a period of time ranging from about 25 to about 35 days.

The method may further comprise administering the pheromone composition to the peri-pubertal suid to induce onset of estrus and continue administration of the composition after onset of estrus in the peri-pubertal suid. The method may further improve performance of the peri-pubertal suid.

Another aspect of the present disclosure encompasses a method of improving performance of a peri-pubertal suid. The method comprises administering a pheromone composition to the suid, the composition comprising a combination of pheromonal agents, wherein the pheromonal agents comprise at least one steroid hormone and one heterocyclic aromatic compound. Improving performance of a peri-pubertal suid may comprise stimulating early onset of estrus in the peri-pubertal suid, stimulating reproductive behavior, synchronizing estrus in the peri-pubertal suid, stimulating weight gain and final weight at market or breeding, increasing feeding behavior, increasing average daily gain, increasing playing behavior, increasing development of ovaries and the reproductive tract, and combinations thereof.

DETAILED DESCRIPTION

Figure 1:
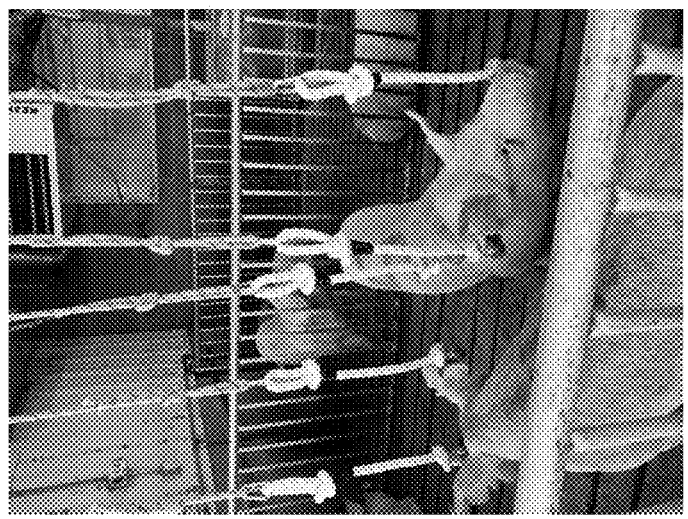
FIG. 1 is a photograph depicting the experimental setup wherein peri-pubertal females are exposed to a pheromone composition by hanging ropes in pens containing peri-pubertal suids. The ropes have the pheromone composition on the tips for the peri-pubertal pigs to smell.

The composition of the present disclosure comprises a combination of pheromone and aromatic compounds, the combination collectively referred to herein as "pheromonal agents", which has been found to be useful and effective in inducing early estrus in peri-pubertal suids, thereby reducing labor, and improving human safety when peri-pubertal pigs are managed. Advantageously, the pheromone agents have also been found to be useful in improving performance of the peri-pubertal gilts.

Additional embodiments and features are set forth in part in the description that follows, and in part will become apparent to those skilled in the art upon examination of the specification, or may be learned by the practice of the embodiments discussed herein. A further understanding of the nature and advantages of certain embodiments may be realized by reference to the remaining portions of the specification, the drawings, the chemical structures, and descriptions, which form a part of this disclosure. Any description of any R-group or chemical substituent, alone or in any combination, may be used in any chemical formula described herein, and formulae include all conformational and stereoisomers, including diastereomers, epimers, and enantiomers. Moreover, any feature of a composition disclosed herein may be used in combination with any other feature of a composition disclosed herein.

I. Pheromone Composition

The pheromonal agents used in the compositions of the present invention comprise at least one steroid hormone. Steroid hormones can be grouped into five groups based on the receptors to which they bind: glucocorticoids, mineralocorticoids, androgens, estrogens, and progestogens. Steroid hormones useful in the present invention may be natural or synthetic.

Generally, the amount of steroid hormone present in the formulation is at least about 0.0000001% (w/w) of the total composition. In one embodiment, the concentration of steroid hormone present in the composition ranges from between about 0.0000001% to about 10% (w/w). In another embodiment, the concentration of steroid hormone present in the composition ranges from between about 0.0001% to about 5% (w/w). Preferably, the concentration of steroid hormone present in the composition ranges from between about 0.0001% to about 1% (w/w), and most preferably the concentration of steroid hormone present in the composition ranges from between about 0.0007% to about 0.0009% (w/w). Also preferably, the concentration of steroid hormone present in the composition ranges from between about 0.0005% to about 0.5% (w/w), and most preferably from between about 0.0005% to about 0.01% (w/w), or from about 0.002% to about 0.006% (w/w).

Preferably, the steroid hormone comprises at least one androgen steroid, which may be selected from the group consisting of androstenone, androstenol, androstadienone, estratetraenol, and combinations thereof. Preferably, the androgen steroid is a combination of androstenone and androstenol. When the androgen steroid is a combination of androstenone and androstenol, the concentration of androstenone present in the composition ranges from between about 0.0001% to about 0.0008% (w/w), and the concentration of androstenol present in the composition ranges from between about 0.0001% to about 0.0008% (w/w). Preferably, the concentration of androstenone present in the composition ranges from between about 0.0002% to about 0.0006% (w/w), more preferably from between about 0.0003% to about 0.0005% (w/w). Also preferably, the concentration of androstenone present in the composition ranges from between about 0.0005% to about 0.009% (w/w), more preferably from between about 0.001% to about 0.003% (w/w). Preferably, the concentration of androstenol present in the composition ranges from between about 0.0002% to about 0.0006% (w/w), more preferably from between about 0.0003% to about 0.0005% (w/w). Also preferably, the concentration of androstenol present in the composition ranges from between about 0.0005% to about 0.009% (w/w), more preferably from between about 0.001% to about 0.003% (w/w).

The pheromonal agents present in the composition additionally comprise an aromatic heterocyclic compound. The amount of aromatic heterocyclic compound present in the formulation is at least 0.0000001% (w/w) of the total composition. In one embodiment, the concentration of aromatic heterocyclic compound in the total composition ranges from between about 0.0000001% to about 10% (w/w). In another embodiment, the concentration of aromatic heterocyclic compound in the total composition ranges from between about 0.0001% to about 5% (w/w). Preferably, the concentration of aromatic heterocyclic compound present in the total composition ranges from between about 0.0001% to about 1% (w/w), preferably from between about 0.0002% to about 0.0006% (w/w), and most preferably the concentration of aromatic heterocyclic compound in the composition ranges from between about 0.0003% to about 0.0005% (w/w). Also preferably, the concentration of aromatic heterocyclic compound in the total composition ranges from between about 0.0005% to about 0.009% (w/w), more preferably from between about 0.001% to about 0.003% (w/w).

A preferred aromatic heterocyclic compound for use in the present invention is quinoline. Preferably, the concentration of quinoline present in the composition ranges from between about 0.0002% to about 0.0006% (w/w) of the total composition, and most preferably from between about 0.0003% to about 0.0005% (w/w) of the total composition. Also preferably, the concentration of quinoline present in the composition ranges from between about 0.0005% to about 0.0009% (w/w), more preferably from between about 0.001% to about 0.004% (w/w).

The pheromonal agents may be formulated with a solvent to form a liquid solution. Liquid solutions may be further prepared in various formulations suitable for delivery to the suid by inhalation. For example, liquid solutions can be further prepared according to methods well known in the art into formulations suitable for use in a pump spray, aerosol, gel, foam, cream, lotion, or diffuser. For instance, the pheromonal agents may be combined with one or more additional components such as solvents, propellants, surface-active agents, emulsifiers or thickeners, foaming agents, preservatives, and fragrances to prepare the various formulations.

Preferably, the composition further includes at least one carrier solvent. Suitable carrier solvents are generally known within the art and are recognized to include lipophilic organic diluents, alcohols, ethylene glycol, propylene glycol, dipropylene glycol, ether, chloroform, benzene, carbon disulfide, oils including non-volatile and volatile liquids and oils, water, and combinations thereof. Suitable alcohols include ethanol, propanol, isopropanol, butanol, pentanol, hexanol, heptanol, octanol, and phenyl ethyl alcohol. In one embodiment, the alcohols may comprise ethanol, isopropanol, butanol, and phenyl ethyl alcohol.

An alcohol solvent may be combined with water or a lipophilic organic diluent or carrier such as ethylene glycol, propylene glycol, dipropylene glycol, dipropylene glycol monoethyl ether, dipropylene glycol methyl ether, or Dow Corning® Q7-9180 silicone liquid. In an exemplary embodiment, the solvent may be a combination of water and an alcohol selected from ethanol or isopropanol. In one embodiment, the amount of solvent present in the composition may range from between about 0.5% and about 99.99% (w/w) of the total composition. The amount of water present in the composition may range from between about 70% and about 99.99% (w/w) of the total composition, for example between about 80% and about 98.5% (w/w) of the total composition. The amount of alcohol present in the composition may range from between about 1% and about 20% (w/w) of the total composition, for example from between about 1.5% and about 10% (w/w) of the total composition.

When the solvent is a combination of water and an alcohol, the solvent preferably comprises water and isopropanol. The concentration of isopropanol may range from between about 1% and about 20% (w/w) of the total composition, preferably from between about 1.5% and about 10% (w/w) of the total composition, more preferably from between about 3% to about 7% (w/w) of the total composition. The amount of water may range from about 0.5% to about 99.99% (w/w) of the total composition. Preferably, the amount of water present in the composition may range from between about 70% and about 99.99% (w/w) of the total composition, more preferably between about 80% and about 98.5% (w/w) of the total composition, more preferably between about 89% and about 93% (w/w) of the total composition.

The compositions may additionally include a propellant. Suitable propellants include dimethyl ether (DME), chlorofluorocarbons (CFC) such as trichloromonofluoromethane, dichlorodifluoromethane, and dichlorotetrafluoroethane; hydrochlorofluorocarbons (HCFC) or hydrofluorocarbons (HFC) such as chlorodifluoromethane, trifluoromonofluoroethane, chlorodifluoroethane, difluoroethane, and heptafluoropropane; hydrocarbons such as propane, butane, and isobutene; and other compressed gases such as nitrogen, carbon dioxide, and nitrous oxide, as well as combinations of any of the above-described propellants. In one embodiment, the propellant may be propane. In another embodiment, the propellant may be 1,1-difluoroethane. The propellant may not comprise an inert gas of the tumorigenic compound class, which includes 1,1,1,2-tetrafluoroethane, chlorodifluoromethane, and dichlorodifluoromethane. The propellant may have a flashpoint of less than about −50° C. Generally, when a propellant is included in the composition, such may range from between about 75% to about 99.99% (w/w) of the total composition, for example between about 85% and about 99.99% (w/w) of the total composition, or between about 95% and about 99.99% (w/w) of the total composition.

The compositions may optionally include one or more surfactants. Surfactants are generally used to prepare compositions formulated as emulsions. Either water-in-oil or oil-in-water emulsions may be formulated. Examples of suitable surfactants include nonionic ethoxylated and non-ethoxylated surfactants, abietic acid, almond oil PEG, beeswax, butylglucoside caprate, $C_{18}$-$C_{36}$ acid glycol ester, $C_9$-$C_{15}$ alkyl phosphate, caprylic/capric triglyceride PEG-4 esters, ceteareth-7, cetyl alcohol, cetyl phosphate, corn oil PEG esters, DEA-cetyl phosphate, dextrin laurate, dilaureth-7 citrate, dimyristyl phosphate, glycereth-17 cocoate, glyceryl erucate, glyceryl laurate, hydrogenated castor oil PEG esters, isosteareth-11 carboxylic acid, lecithin, lysolecithin, nonoxynol-9, octyldodeceth-20, palm glyceride, PEG diisostearate, PEG stearamine, poloxamines, polyglyceryls, potassium linoleate, PPG's, raffinose myristate, sodium caproyl lactylate, sodium caprylate, sodium cocoate, sodium isostearate, sodium tocopheryl phosphate, steareths, TEA-$C_{12}$-$C_{13}$ pareth-3 sulfate, tri-$C_{12}$-$C_{15}$ pareth-6 phosphate, and trideceths.

In certain applications, it may be desirable to thicken the composition. Suitable thickening or viscosity-increasing agents include acrylamides copolymer, agarose, amylopectin, bentonite, calcium alginate, calcium carboxymethyl cellulose, carbomer, carboxymethyl chitin, cellulose gum, dextrin, gelatin, hydrogenated tallow, hydroxyethylcellulose, hydroxypropylcellulose, hydroxypropyl starch, isopropyl palmitate, magnesium alginate, methylcellulose, microcrystalline cellulose, pectin, various PEGs, polyacrylic acid, polymethacrylic acid, polyvinyl alcohol, various PPGs, sodium acrylates copolymer, sodium carrageenan, xanthan gum, and yeast beta-glucan. When present, the amount of thickener may range from between about 1% to about 30% (w/w) of the total composition, for example between about 5% to about 20% (w/w) of the total composition, or from between about 10% to about 15% (w/w) of the total composition.

The compositions may additionally comprise an emulsifier or thickening agent, such as distilled mono and di-glycerides, propylene glycol monoesters, sodium stearoyl-2-lactylate, polysorbate 60, lecithin, hydroxylated lecithin, lanolin, and any other emulsifier known and used in the industry.

The compositions may additionally comprise a fragrance. The fragrance may be any fragrance that provides a desired odor-masking effect without substantially interfering with the essential properties of the composition. Although a variety of fragrances may be employed without departing from the scope of the present disclosure, suitable fragrances include floral essences, citrus blossoms, oil or extracts of conifers, or spices. Examples of floral essences include rose, lilac, lavender, *gardenia*, and jasmine. Suitable citrus blossoms include orange and lemon, and suitable oil or extracts of conifers include pine and juniper. Generally, fragrances may comprise between about 0.25% and about 1% (w/w) of the total composition.

The compositions may further comprise an edible dye. By coloring the invention, it allows the producer to quickly identify which animals have self-administered or it will indicate that an animal was sprayed and the spray reached the nostrils.

In some embodiments, the pheromonal agents are dissolved or diluted with a solvent and a thickener to form a solution for use in a diffuser. An exemplary diffuser solution may comprise between about 0.0009% to about 0.0014% (w/w) pheromonal agents, between about 80% to about 85% (w/w) solvent, and between about 10% to about 20% (w/w) thickener.

In other embodiments, the pheromonal agents are dissolved or diluted in a nonaqueous organic solvent or solvent mixture to form a solution for incorporation into a pump spray. An exemplary pump spray solution may comprise about 0.0009% to about 0.0014% (w/w) pheromonal agents, about 4% to about 6% (w/w) isopropyl alcohol, about 2% to about 5% (w/w) lanolin oil, and about 89% to about 93% (w/w) water. Alternatively, the pheromone composition is formulated as a spray composition comprising about 0.001% to about 0.003% (w/w) androstenone, about 0.001% to about 0.003% (w/w) androstenol, about 0.001% to about 0.003% (w/w) quinolone, about 4% to about 6% (w/w) isopropyl alcohol, about 2% to about 5% (w/w) lanolin oil, and about 89% to about 93% (w/w) water. Additionally, about 0.15% to about 0.35% (w/w) of a preservative may be added to the solution.

In some embodiments, the pheromonal agents are formulated as foaming compositions. Foaming compositions suitable for use in a formulation of the disclosure are known in the art. Foaming formulations may comprise, in addition to the pheromonal agents and solvents, a foaming agent or surfactant. A foam stabilizer may optionally be included. An optional foam stabilizer ingredient (mentioned above), if present, is preferably present in an amount effective to further stabilize the foam. A foaming agent or surfactant may suitably be selected from the group consisting of a nonionic surfactant, an ionic surfactant, an amphoteric surfactant, and commercially-available mixtures thereof. An amphoteric surfactant (such as baby-type shampoo) is a surfactant that can function as an anionic surfactant or as a cationic surfactant, depending upon the pH of the medium or system within which the amphoteric surfactant is contained. Moreover, a number of commercially-available emulsifier compositions, some of which are known in the art as "Triton X-100", "Triton X-193" and the like, are illustrative of suitable foaming agent, for purposes of the present invention. Additional suitable foaming agents include synthetic anionic detergents, such as soap systems based upon neutralized carboxylic acids, alkyl aryl sulfonates, alpha-olefin sulfonates, alkyl sulfonates or sulfates, and the like. Also suitable as foaming agents are nonionic surfactants such as ethoxylated alcohols, alkylphenol ethoxylates, and the like. In a preferred alternative of the embodiments, a foaming agent is an ethoxylated alcohol. Non-limiting examples of ethoxylated alcohols include cetearyl alcohol ethoxylates, cetyl alcohol ethoxylates, cetyl oleyl alcohol ethoxylates, lauryl alcohol ethoxylates, stearyl alcohol ethoxylates, isodecyl alcohol ethoxylates, isotridecyl alcohol ethoxylates, C9-C12 synthetic alcohol ethoxylates, and combinations therefore. Preferably an ethoxylated alcohol is Surfonic® L12-6, a six-mole ethoxylate of linear, primary 10-12 carbon number alcohol.

Foaming formulations generally comprise, in addition to the pheromonal agents, a foaming agent or surfactant, lubricants, and propellants. Suitable propellant may be as described herein above. Preferably, a propellant is a liquefied petroleum propellant, preferably Aeron® NP-46.

A preferred foaming formulation of the pheromonal agents may comprise between about 0.004% to about 0.008% (w/w) pheromonal agents, between about 1% to about 5% (w/w) Surfonic L12-6 foaming agent, between about 1% to about 10% (w/w) glycerin lubricant, between about 70% to about 95% (w/w) water, and between about 5% to about 20% (w/w) Aeron NP-46 propellent. Alternatively, a preferred foaming formulation of the pheromonal agents may comprise between about 0.0009% to about 0.0014% (w/w) pheromonal agents, between about 1% to about 5% (w/w) Surfonic L12-6 foaming agent, between about 1% to about 10% (w/w) glycerin lubricant, between about 70% to about 95% (w/w) water, and between about 5% to about 20% (w/w) Aeron NP-46 propellent.

In yet other embodiments, pheromonal agents may be microencapsulated. As will be appreciated by a skilled artisan, the encapsulation or coating method can and will vary depending upon the pheromonal agents used to form the composition and coating, and the desired physical characteristics of the microcapsules themselves. Microcapsule particles may be uniform in size/dimension or, alternatively, may be varying in size/dimension. More than one encapsulation method may be employed so as to create a multi-layered microcapsule, or the same encapsulation method may be employed sequentially so as to create a multi-layered microcapsule. Suitable methods of microencapsulation may include spray drying, spinning disk encapsulation (also known as rotational suspension separation encapsulation), supercritical fluid encapsulation, air suspension microencapsulation, fluidized bed encapsulation, spray cooling/chilling (including matrix encapsulation), extrusion encapsulation, centrifugal extrusion, coacervation, alginate beads, liposome encapsulation, inclusion encapsulation, colloidosome encapsulation, sol-gel microencapsulation, and other methods of microencapsulation known in the art. Pheromonal agents may also be incorporated into a polymeric matrix, which is then processed into molded particles comprising the pheromone composition using standard methods known in the art, the molded particles being formed, for example, into pellets, spheres, microspheres, beads, microbeads, bubbles, microbubbles, flakes, granules, or other molded particle.

Irrespective of the method of formulating a composition, the composition may be formulated for suitable release characteristics such that the pheromone composition can be slowly released over an extended period of time for inhalation by the target animal. A composition may be slowly released over a duration of time ranging from about 10 to about 50 days or a duration of time ranging from about 25 to about 35 days. Methods of formulating composition for extended release are known in the art.

In some embodiments, compositions for the inducement of reproductive behavior in female suids may be as described in U.S. Pat. No. 9,480,689, the disclosure of which is incorporated herein in its entirety. Preferably, the pheromone composition is formulated as a spray composition comprising about 0.0003% to about 0.0005% (w/w) androstenone, about 0.0003% to about 0.0005% (w/w) androstenol, about 0.0003% to about 0.0005% (w/w) quinolone, about 3% to about 7% (w/w) isopropanol, and about 89% to about 93% (w/w) water. Alternatively, the pheromone composition is formulated as a spray composition comprising about 0.001% to about 0.003% (w/w) androstenone, about 0.001% to about 0.003% (w/w) androstenol (w/w), about 0.001% to about 0.003% quinolone, about 3% to about 7% (w/w) isopropanol, and about 89% to about 93% (w/w) water.

II. Administration

Mammals, including pigs and other suids, have several anatomical organs that receive olfactory signals. The two most dominant "smell" organs are the main olfactory epithelium (MOE) and the vomeronasal organ (VNO). Other sensory fibers in the nasal cavity can sense odors, but the main olfactory bulb and accessory olfactory bulb (receiving signals from the VNO) are the major integrating systems.

The olfactory bulb lies at the front of the brain. It sends neuronal projections through a bone and extends these projections into the olfactory epithelium. The MOE is an extensive area with a rich blood supply and mucosa in which odor aerosol molecules pass on their way to the lungs. Odor or water droplets will settle on the MOE, and if an odor receptor is present, that odor receptor will be bound and cause activation of the sensory neurons.

Administration of the composition to a subject peri-pubertal gilt is typically accomplished through any method allowing for delivery of an effective amount of the composition to the olfactory system for an effective period of time. Such methods of administration include, for example, placing or distributing the composition in the environment of the suid, either by applying (e.g., spraying or wiping) the composition to surfaces in the living environment of the suid, or directly onto the suid, such as to its facial region, snout, or head. For example, the pheromone composition may be administered topically to a suid using an aerosol, pump spray, foam, collar, wipe, dip, liquid, gel, lotion, and/or cream. Alternatively, the pheromone composition may be administered by placing the composition in the environment of the suid by providing a liquid diffuser in the environment of the suid. Preferably, the composition is administered to the olfactory system of a subject peri-pubertal gilt via inhalation by the animal, preferably by applying the composition to a rope in the environment of the suid that allows the pigs to self-administer the composition. Further, the pheromone compositions may be administered simultaneously to a number of peri-pubertal suids. Alternatively, a pheromone composition may be administered individually to a peri-pubertal pig.

Pheromone compositions may be administered to peri-pubertal suids until onset of estrus. Alternatively, the compositions may be administered after onset of estrus in the peri-pubertal suid. Additionally, the compositions may be administered to peri-pubertal pigs until onset of estrus and after onset of estrus in the peri-pubertal gilt. For instance, the pheromone compositions may be administered to peri-pubertal suids to induce onset of estrus, and continue to be administered after onset of estrus in the peri-pubertal suid.

The term "effective amount" describes an amount of pheromonal agent present in a composition sufficient to produce a noticeable effect, for example the onset of estrus in the subject suid or engaging in reproductive behaviors by the subject suid upon administration to the subject, as determined according to behavioral observations described herein. The term "effective period of time" describes a period of time during which an animal is exposed to the pheromonal composition sufficient to produce a noticeable effect as described. An effective period of time may be until administration of the pheromonal agents produces a noticeable effect, or may also extend beyond the period of time required to produce the noticeable effects. As it will be recognized by individuals of skill in the art, the effective amount and duration will depend on factors such as individual animal parameters including age, physical condition, size and weight; concurrent treatments; the frequency of treatment; the composition of the pheromonal agent; or the mode of administration. These factors are well known to those of ordinary skill in the art.

It should be understood that the combination of pheromonal agents used in the composition may be provided in the form of pure concentrate (100% concentration) or a diluted composition with additional excipients in the dosage form (i.e., the amount of active ingredient in the composition is less than or equal to 99.99%, and the remainder consists of inactive excipients). If diluted, the amount of pheromonal agents dispensed in the various dosage forms may range from between about 1.0 pg/mL to about 1.0 g/mL, such as between about 1.0 ng/mL to about 1.0 g/mL. One of skill in the art will appreciate that the volume of active component added to the composition will need to be adjusted to account for the dilution and to ensure the end composition comprises the appropriate final concentration of pheromonal agents. The various components of the composition may be provided in a variety of dosage forms including, but not limited to, liquid solution or suspension, emulsion, aerosol, and the like.

When the pheromone composition is formulated as a spray composition for self-administration by the animal by placing the composition in the environment of the suid, an effective amount of the composition may range from about 0.1 ml to about 100 ml of the composition administered daily for an effective period of time ranging from about 1 second, one hour, one day, one week, or about 4 months or longer. When an effective period of time extends beyond the period of time required to produce the noticeable effects, the period of time may extend about 1 second, one hour, one day, one week, or about 4 months or longer.

When the pheromone composition is formulated as a spray composition for self-administration comprising about 0.0003% to about 0.0005% (w/w) androstenone, about 0.0003% to about 0.0005% (w/w) androstenol, about 0.0003% to about 0.0005% (w/w) quinolone, about 3% to about 7% (w/w) isopropanol, and about 89% to about 93% (w/w) water, an effective amount of the composition may range from about 1 ml to about 10 ml of the composition administered daily for a period of time ranging from about 10 days to about 3 months. Preferably, about 2 ml to about 6 ml, more preferably 3 ml to about 5 ml of the composition is administered daily for a period of time ranging from about 20 days to about 40 days, more preferably for a period of time ranging from about 10 days to about 50 days, by placing the composition in the environment of the suid that allows the pigs to self-administer the composition.

III. Methods of Using

In some aspects, the present disclosure is directed to methods of using a pheromone composition to induce or stimulate early onset of estrus in a peri-pubertal suid, thereby reducing labor, and improving human safety when peri-pubertal pigs are managed. The present disclosure is further directed to methods of improving performance of the peri-pubertal gilts by stimulating early onset of estrus in the peri-pubertal pig, stimulating reproductive behavior, synchronizing estrus in the peri-pubertal gilt, stimulating weight gain and final weight at market or breeding, increasing feeding behavior, increasing average daily gain, increasing playing behavior, increasing development of ovaries and the reproductive tract, and combinations thereof. Other methods of using a pheromone composition to stimulate reproductive behavior and increase reproductive success in a post-pubertal suid may be as described in U.S. Pat. No. 9,480,689, the disclosure of which is incorporated herein in its entirety.

The methods comprise administering an effective amount of the pheromone composition to a peri-pubertal suid until onset of estrus, after onset of estrus in the adult gilt, and combinations thereof. In some embodiments, a method comprises administering the pheromone composition to peri-pubertal suids to induce onset of estrus and continue administration of the composition after onset of estrus in the peri-pubertal suid. The pheromone composition may be as described in Section I above. Administering a composition comprising a combination of pheromonal agents may be as described in Section II above.

DEFINITIONS

Unless otherwise defined, all technical and scientific terms used herein have the same meaning as is commonly understood by one of skill in the art to which this disclosure belongs at the time of filing. If specifically defined, then the definition provided herein takes precedent over any dictionary or extrinsic definition. Further, unless otherwise required by context, singular terms shall include pluralities, and plural terms shall include the singular. Herein, the use of "or" means "and/or" unless stated otherwise. All patents and publications referred to herein are incorporated by reference.

"Suid" refers to any member of the family Suidae, hoofed mammals, order Artiodactyla, including the wild and domestic pigs, babirusas, boars, bush pigs, swine, and warthogs. Suids are stout animals with small eyes and coarse, sometimes sparse, hair. All have muzzles ending in a rounded cartilage disk used to dig for food. Some species have tusks. Suids are omnivorous and usually gregarious.

"Pheromonal agents" refers to a combination of pheromone and aromatic compounds in specific amounts which have been found to be useful and effective in inducing or stimulating reproductive behavior in female suids. Specifically, the term "pheromonal agents" as used herein refers to the combination of at least one steroid hormone, preferably androstenone and androstenol, with at least one aromatic heterocyclic compound, preferably quinoline.

As used herein, the term "adult female suid" refers to a female pig older than or after she weans her first litter. Further, as used herein, the term "gilt" refers to a female pig from birth until she has weaned her first litter.

As used herein, the terms "peri-pubertal suid," "peri-pubertal pig," and "peri-pubertal gilt" are used interchangeably, and refer to a gilt of an age where the gilt is capable of first estrous upon exposure to an adult boar, or to a pheromone composition of the invention. In general, a peri-pubertal suid may be about 4 to about 12 months of age, preferably about 5 to about 8 months of age.

As used herein, the term "early estrus" refers to an onset of estrus in animals treated with the pheromone composition that occurs at a significantly earlier age when compared to untreated animals. In general, onset of estrus in animals treated with the pheromone composition occurs (or is accelerated by) days, weeks, or months earlier when compared to onset of estrus in animals that are not treated with the pheromone composition. In general, onset of estrus in animals treated with the pheromone composition is accelerated by about 10-90 days when compared to onset of estrus in animals that are not treated with the pheromone composition, preferably by about 20 to 40 days, and more preferably by about 30 days when compared to onset of estrus in animals that are not treated with the pheromone composition.

When introducing elements of the present disclosure or the embodiments(s) thereof, the articles "a," "an," "the," and "said" are intended to mean that there are one or more of the elements. The terms "comprising," "including," and "having" are intended to be inclusive and mean that there may be additional elements other than the listed elements.

Although the disclosure described herein is susceptible to various modifications and alternative iterations, specific embodiments thereof have been described in greater detail above. It should be understood, however, that the detailed description is not intended to limit the disclosure to the specific embodiments disclosed. Rather, it should be understood that the disclosure is intended to cover all modifications, equivalents, and alternatives falling within the spirit and scope of the disclosure as defined by the claim language.

EXAMPLES

While the present invention is disclosed in reference to the preferred embodiments or examples above, it is to be understood that these embodiments or examples are intended for illustrative purposes, which shall not be treated as limitations to the present invention. It is contemplated that modifications and combinations will readily occur to those skilled in the art, which modifications and combinations will be within the spirit of the invention and the scope of the following claims.

Example 1. Preparation of Spray Composition Comprising Pheromonal Agents

A pump spray formulation comprising the combination of pheromonal agents androstenone, androstenol, and quinoline was prepared in accordance with the formulation set forth in Table 1.

determine if administering the pheromone formulation to peri-pubertal pigs could effectively cause peri-pubertal suids to become sexually developed earlier, and thereby allowing for earlier induction of peri-pubertal suids into the breeding herd.

The efficacy of the spray composition containing androstenone, androstenol, and quinoline was tested at a research pig farm. Farm workers were instructed to isolate peri-pubertal suids that are of a certain age into two groups: a treatment group and a control group. The treatment group of peri-pubertal suids was then exposed to the pheromone composition through hanging ropes (toys) dipped in the pheromone composition and hung at an appropriate height in the pen comprising the treatment peri-pubertal suids (FIG. 1). Peri-pubertal suids in the control group were not exposed to the pheromone composition.

Figure 2:
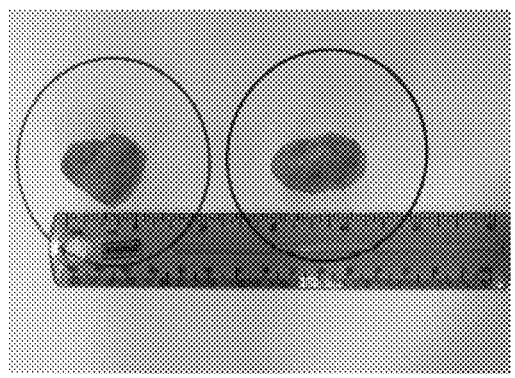
FIG. 2 is a photograph depicting ovaries from a peri-pubertal suid in the control group.
Figure 3:
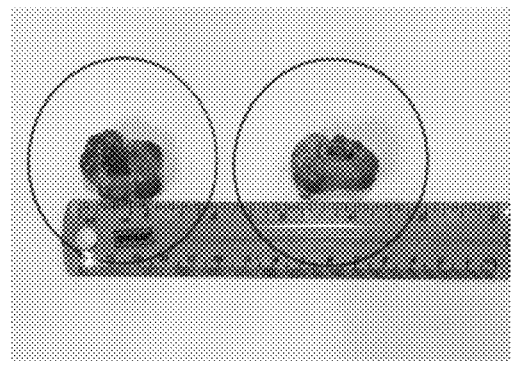
FIG. 3 is a photograph depicting ovaries from a peri-pubertal pig in the group receiving a pheromone treatment.
Figure 4:
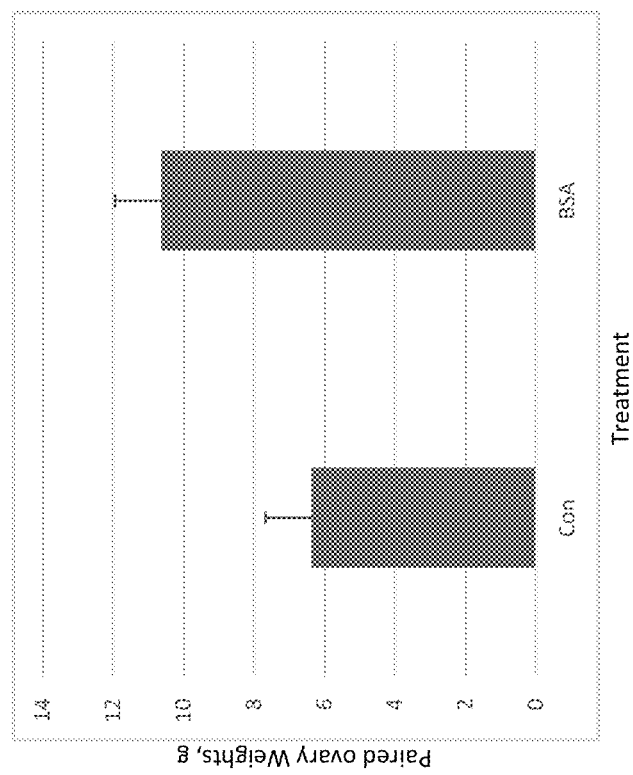
FIG. 4 is a histogram depicting the average weight of paired ovaries of animals in the control group (Con) and animals receiving a pheromone treatment (BSA). ($P<0.05$; $N=4$)

A total of 4 peri-pubertal suids were tested for each treatment. The peri-pubertal suids were all of the same age (about 5 months of age) at first exposure. The treatment process was continued for 30 days. All animals were monitored for estrus by taking them through humane slaughter and observing the weight and structure of their ovaries. The live weight of the animals was also monitored for the duration of the experiment. After 30 days, the animals were sacrificed and their ovaries removed. The paired ovaries of each animal were then weighed and the sizes measured (FIGS. 2-4). The results are shown in Table 2.

TABLE 2

Results.

| Treatment | Average live weight of animals (Kg) | Average Ovary Morphology | Average paired ovary weight (g) | Number of peri-pubertal suids with estrous |
|---|---|---|---|---|
| Pheromone treated (N = 4) | 119 | Larger, many follicles were observed* | 10.2* | 4 |
| Control (N = 4) | 138.5 | Small, no follicles | 6.1 | 0 |

*Indicates a significant difference

TABLE 1

Pump Spray Composition.

| Component | % | grams |
|---|---|---|
| Androstenone | 0.0004 | 0.0004 |
| Androstenol | 0.0004 | 0.0004 |
| Quinoline | 0.0004 | 0.0004 |
| Isopropyl Alcohol | 5.0000 | 5.0000 |
| Lanolin Oil | 3.5000 | 3.5000 |
| Preservative | 0.2500 | 0.2500 |
| D.I. water | 91.2490 | 91.2490 |
| Total | 100.0000% | 100.0000 |

Example 2. Determining the Efficacy of a Spray Composition Containing Androstenone, Androstenol, and Quinoline to Stimulate Early Onset of Estrus in Peri-Pubertal Pigs This study evaluated the formulation of Example 1 to determine its efficacy at induction of early onset of estrous in peri-pubertal pigs. The objective of this study was to These results illustrate that the present invention is effective in inducing early onset of estrus in peri-pubertal gilts, which in turn increases productivity.

Figure 5:
FIG. 5 is a photograph depicting the experimental setup showing control peri-pubertal gilts.

Example 3. Determining the Efficacy of a Spray Composition Containing Androstenone, Androstenol, and Quinoline to Stimulate Weight Gain in Peri-Pubertal Pigs This study evaluated the formulation of Example 1 to determine its efficacy at enhancing weight gain in peri-pubertal gilts. The efficacy of the spray composition containing androstenone, androstenol, and quinoline was tested at a research pig farm. Peri-pubertal suids were randomly assigned to treatments when they were younger than 4 months of age. Peri-pubertal suids were housed 4 per pen. All treatment pens were 7×12 feet in dimension (21 ft$^2$/pig). Each pen had a 2-hole feeder and a nipple waterer. Control peri-pubertal suids were managed according to standard farm practices (FIG. 5). Treated pens had cotton ropes hanging where the peri-pubertal suids could touch and manipulate the ropes.

Figure 6:
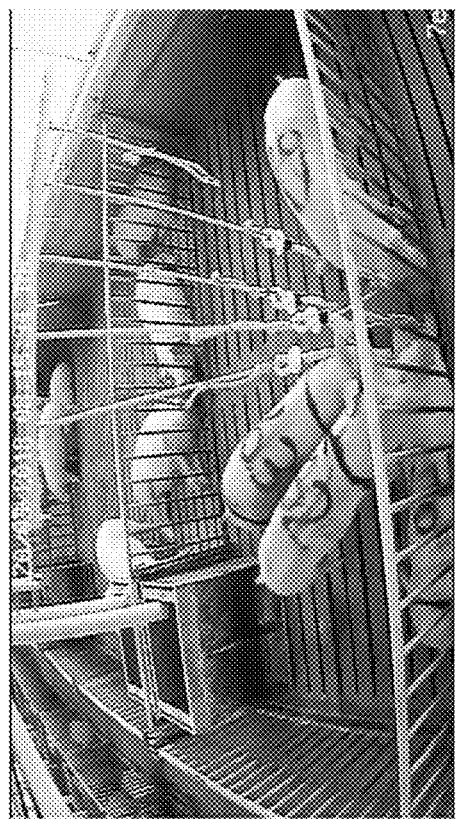
FIG. 6 is a photograph depicting the experimental setup wherein peri-pubertal suids are exposed to a pheromone composition by hanging ropes in pens containing peri-pubertal gilts. The ropes have the pheromone composition on the tips for the peri-pubertal pigs to smell.

Thirty days before anticipated marketing (when the peri-pubertal suids were about 6 months of age), peri-pubertal suids in the treatment pens were exposed to the cotton ropes that were sprayed with the pheromone formulation (FIG. 6). A spray of 4 mL of the formulation was administered daily during the 30-day study. Peri-pubertal suids were weighed at the start of the study and again at the end (30 days later). Average Daily Gain (ADG) was calculated for each pig and for each pen of pigs.

The results of the live body weight at 6 months of age are shown in Table 3. When peri-pubertal suids had exposure to pheromone-ropes and were able to self-administer the pheromone formulation while they played with the rope, it caused peri-pubertal suids to be heavier. Thirty days of pheromone-rope exposure increased peri-pubertal suid body weights by 11.9 kg or 10% on average. Peri-pubertal suids averaged 76 kg when put on test; then they were not handled until the final weight was collected. The live weights of the peri-pubertal suids were heavier (P<0.05) after 30 days exposure to pheromone-ropes.

TABLE 3

| Group | TRT | Live weight, kg |
|---|---|---|
| A | CON | 123.5 |
| A | Pheromone treatment | 128.9 |
| B | CON | 115.8 |
| B | Pheromone treatment | 135.1 |
| C | CON | 130.0 |
| C | Pheromone treatment | 143.6 |
| Average | CON | 123.1 |
| Average | Pheromone treatment | 135.9 |
| SD | | 9.56 |
| SE | | 5.53 |
| DIFF | | 12.79 |
| t-value | | 2.32 |
| | | P < 0.05 |

CON: Control

Figure 7:
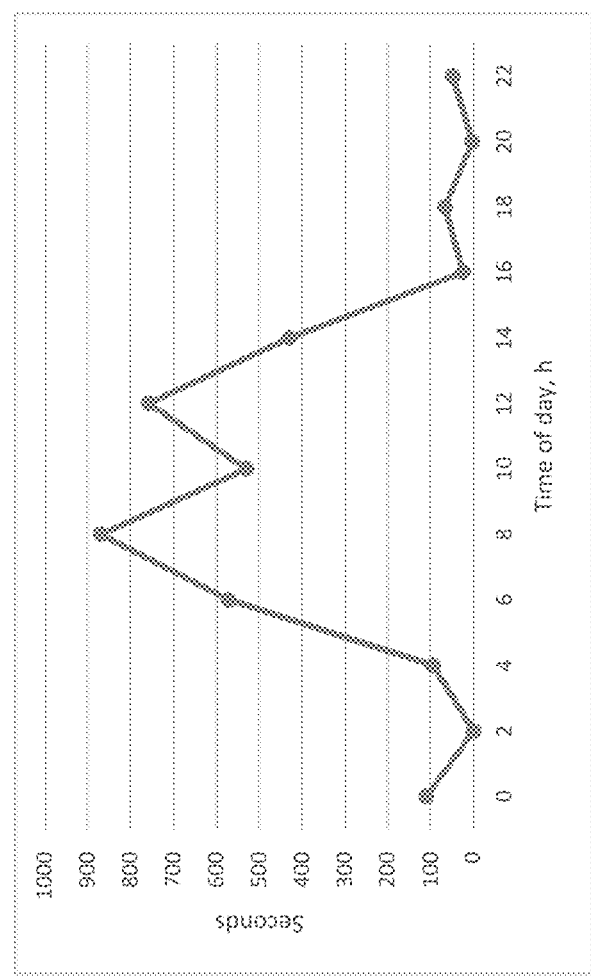
FIG. 7 is a graph depicting time in seconds per 2 hours that 4 peri-pubertal suids interacted (chewed, licked, pulled, or touched) with a pheromone rope over a 24 hour period.

Example 4. Determining the Effect of a Spray Composition Containing Androstenone, Androstenol, and Quinoline on Behavior of Peri-Pubertal Gilts This study evaluated the formulation of Example 1 to determine its effect on behavior in peri-pubertal pigs. In this study, peri-pubertal suid interaction with the toy ropes containing the pheromone formulation was observed for a 24 hour period to determine if each peri-pubertal suid interacted with the pheromone ropes. As shown in FIG. 7, most of the rope interaction occurred during the middle of the day, which also corresponds to the primary feeding activity in peri-pubertal suids. Peri-pubertal suids interacted with the ropes from zero to 3 minutes per hour. Further, every peri-pubertal suid was observed interacting with the pheromone-ropes.

Example 5. Quantifying the Effect of a Spray Composition Containing Androstenone, Androstenol, and Quinoline on Behavior of Peri-Pubertal Pigs During Active Period This study quantified the effect of the formulation of Example 1 on the behavior of peri-pubertal suids during the morning hours when pigs were most active (0800 through 1200 h). The experimental setup was as follows: control (no rope), rope alone, and rope treated with the pheromone formulation. Four ropes were used per pen, with pheromone applied daily where applicable.

As shown in Table 4, peri-pubertal suids with ropes and a control solution (rope alone) manipulated the ropes for the same time as peri-pubertal suids manipulated pheromone-ropes. For both treatment groups, the rope or pheromone-rope increased feeding behavior and reduced inactive behaviors (lying down especially). Thus, the rope caused an increase in both rope play and feeding behaviors. The increased feeding behavior was associated with increased weight gain and a heavier final body weight.

TABLE 4

Quantification of behaviors shown by pigs when experiencing control conditions (no rope or pheromone), rope alone or rope treated with pheromone.

| Behavior | Control | Rope | Rope + BB |
|---|---|---|---|
| Lying down | 82.6* | 47.5 | 49.0 |
| Standing | 4.9 | 1.4 | 3.1 |
| Feeding | 6.9* | 17.4 | 11.1 |
| Drinking water | 0.75 | 0.38 | 1.0 |
| Moving | 1.5 | 1.2 | 0.75 |
| Play (not including rope interactions) | 3.1* | 0.75 | 0.13 |
| Rope interaction | n/a | 31.4 | 34.5 |

Data are % time an average of 4 pigs.
*represents rows in which the control pigs differed from treated pigs. Using BB did not increase or decrease rope manipulation.

Example 6. Quantifying the Effect of a Spray Composition Containing Androstenone, Androstenol, and Quinoline on Growth and Reproductive Development This study quantified the effect of the formulation of Example 1 on the growth and reproductive development of peri-pubertal suids. Pigs were weighed at the start of the random assignment of peri-pubertal suids to treatment pens. Peri-pubertal suids were housed 4 peri-pubertal suids/pen. When ropes were present, 4 ropes were provided (see FIGS. 5 and 6). Starting body weights of peri-pubertal suids were 76.4, 76.9 and 76.9 kg/peri-pubertal suid for control, rope, and pheromone-rope treatment groups. This study had 4 peri-pubertal suids per pen and one pen per treatment. Measures were taken on individual peri-pubertal suids. Data are presented in Table 5 showing how pheromone increased weight gain and final body weight of peri-pubertal suids. All peri-pubertal suids averaged 76 kg 91 days before the final body weight (BW). Pigs with the rope and a placebo spray gained 4.7% more weight, but pheromone-treated peri-pubertal suids gained 18.9% more weight than control (CON) peri-pubertal suids.

TABLE 5

| Treatment | BW, KG | BW, lb | ADG, kg/d | ADG, lb/d | % Diff |
|---|---|---|---|---|---|
| Control | 130.0 | 286.0 | 1.07 | 2.36 | |
| Placebo (rope alone) | 133.0 | 292.6 | 1.12 | 2.47 | 4.7% |
| BB on rope | 143.6 | 316.0 | 1.34 | 2.94 | 18.9% |

Figure 8A:
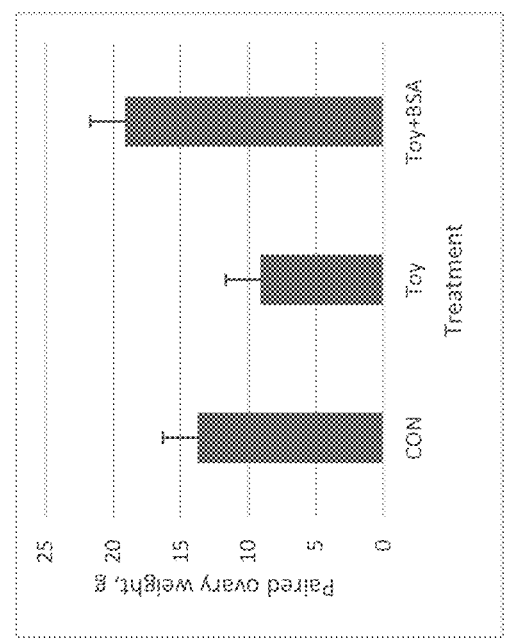
FIG. 8A is a histogram depicting the average weight of paired ovaries of animals in the no toy control group (Con), toy control group (Toy), and animals receiving a pheromone treatment on rope (Toy+BSA). ($P<0.5$)
Figure 8B:
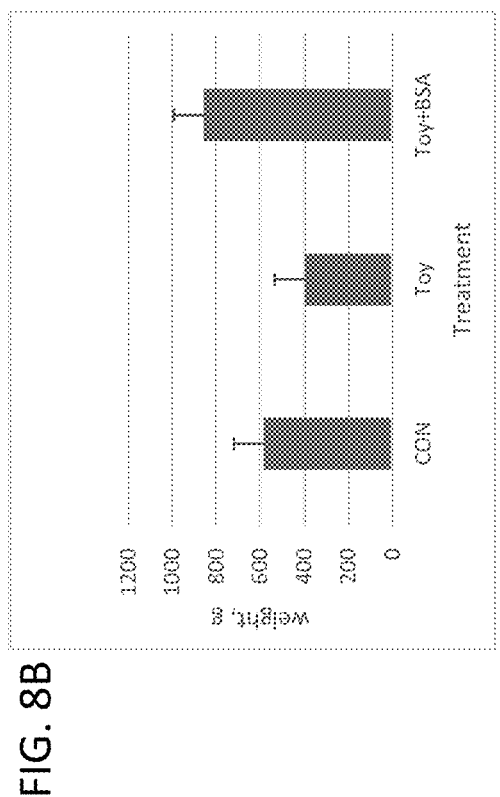
FIG. 8B is a histogram depicting the weight of reproductive tract of animals in the no toy control group (Con), toy control group (Toy), and animals receiving a pheromone treatment on rope (Toy+BSA). ($P<0.5$)
Figure 8C:
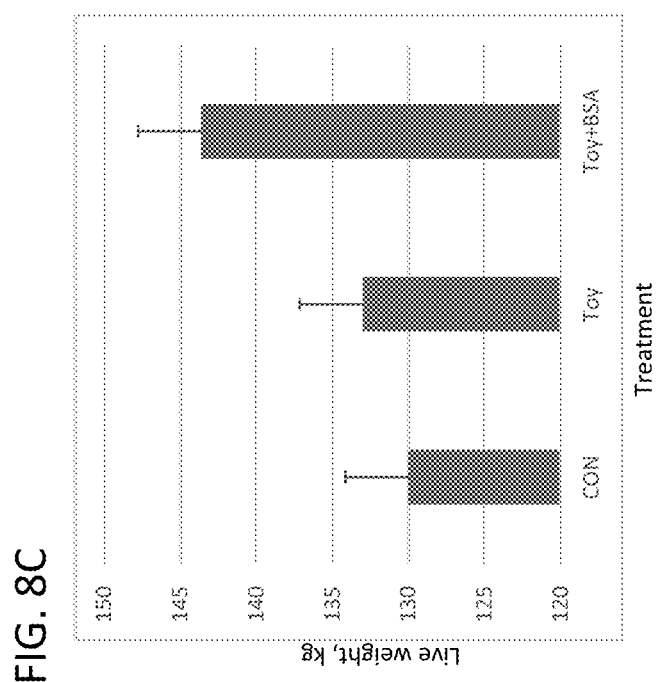
FIG. 8C is a histogram depicting the live weight at slaughter of animals in the no toy control group (Con), toy control group (Toy), and animals receiving a pheromone treatment on rope (Toy+BSA). ($P<0.05$)
Figure 8D:
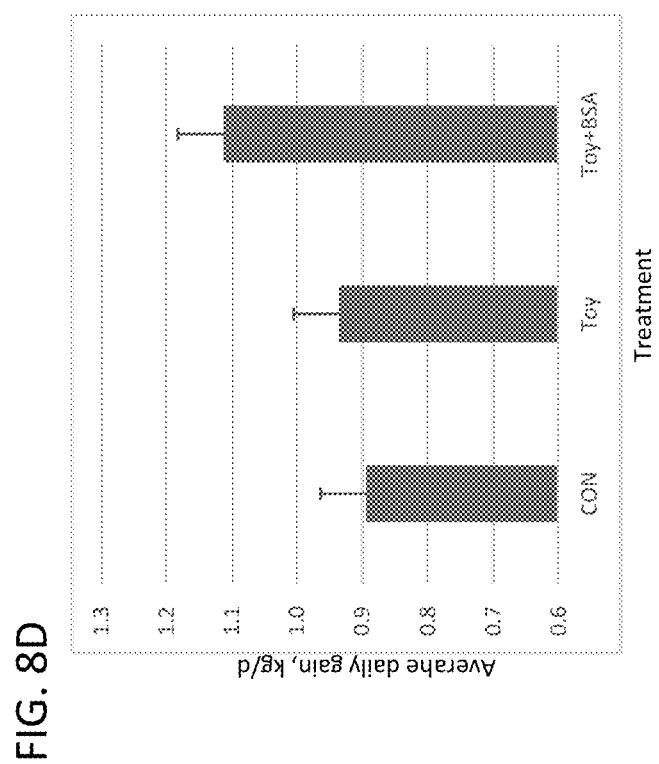
FIG. 8D is a histogram depicting the average daily gain (ADG) of animals in the no toy control group (Con), toy control group (Toy), and animals receiving a pheromone treatment on rope (Toy+BSA). ($P<0.05$)
Figure 9A:
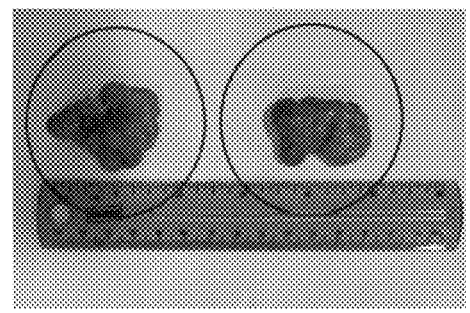
FIG. 9A is a photograph depicting ovaries from a peri-pubertal pig in the group receiving a pheromone treatment.
Figure 9B:
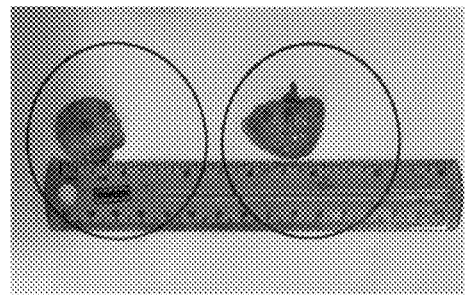
FIG. 9B is a photograph depicting ovaries from a peri-pubertal gilt in the control group not receiving a pheromone treatment.

After exposure to treatments for 30 days, peri-pubertal suids were taken to the Meat Lab for humane slaughter and collection of the reproductive tracts. The entire reproductive tract and ovaries were weighed. Pheromone caused a significant increase in the weight of the ovaries (FIG. 8A) and the reproductive tracts (FIG. 8B). Pictures of example ovaries are shown in FIGS. 9A and 9B. Note the more extensive follicular development in BB-treated peri-pubertal suids. Pheromone caused a 10% increase in body weight at slaughter (FIG. 8C) and a 24% increase in ADG (FIG. 8D). All peri-pubertal suids experiencing pheromone had ovaries that had developed follicles and had one or more estrus cycles prior to harvest. Control peri-pubertal suids were quite variable with 25-100% of ovaries developing visible follicles (about 50% of control peri-pubertal suids on average had visible follicles). The rope alone (with no pheromone) did not increase reproductive tract development or weight gain.

Example 7. Foam Formulation Containing a Pheromonal Composition

A foamable formulation comprising the combination of pheromonal agents androstenone, androstenol, and quinoline was prepared in accordance with the formulation set forth in Table 6.

TABLE 6

Foamable pheromone formulation

| Component | % | Function |
|---|---|---|
| Pheromone blend | 0.006% (0.002 androstenone, 0.002 androstenol, and 0.002 quinoline) | Active ingredient |
| Alcohols, C10-14, ethoxylated Surfonic L12-6 CAS # 66455-15-0 | 2 | Foaming Agent |
| Glycerin CAS # 56-81-5 | 4.5 | Lubricant |
| Deionized Water CAS # 7732-18-5 | 85.494 | Solvent |
| Liquefied Petroleum Gas Aeron NP-46 CAS # 68476-86-8 | 8 | Propellant |

One skilled in the art would readily appreciate that the methods, compositions, and products described herein are representative of exemplary embodiments, and are not intended as limitations on the scope of the disclosure. It will be readily apparent to one skilled in the art that varying substitutions and modifications may be made to the present disclosure without departing from the scope and spirit of the disclosure.

The present disclosure illustratively described herein suitably may be practiced in the absence of any element or elements, limitation or limitations that are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the present disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this disclosure as defined by the appended claims.

What is claimed is:

1. A method of stimulating early onset of estrus in a peri-pubertal suid comprising: administering a pheromone composition to the suid, the composition comprising a combination of pheromonal agents, wherein the pheromonal agents comprise at least one steroid hormone and quinoline.

2. The method of claim 1, wherein the pheromone composition is administered for a period of time ranging from about 25 to about 35 days.

3. The method of claim 1, wherein the steroid hormone is an androgen steroid selected from the group consisting of androstenone, androstenol, androstadienone, estratetraenol, and combinations thereof.

4. The method of claim 3, wherein the androgen steroid is present in an amount from between about 0.0001% to about 1% (w/w) of the composition.

5. The method of claim 3, wherein the androgen steroid consists of androstenone and androstenol.

6. The method of claim 5, wherein the androstenone is present in the composition at a concentration ranging from between about 0.0003% to about 0.0005% (w/w), and the androstenol is present in the composition at a concentration ranging from between about 0.0003% to about 0.0005% (w/w).

7. The method of claim 5, wherein the androstenone is present in the composition at a concentration ranging from between about 0.001% to about 0.003% (w/w), and the androstenol is present in the composition at a concentration ranging from between about 0.001% to about 0.003% (w/w).

8. The method of claim 1, wherein quinoline is present in an amount from between about 0.0007% to about 0.0009% (w/w) of the composition.

9. The method of claim 1, wherein quinoline is present in an amount from between about 0.001% to about 0.003% (w/w) of the composition.

10. The method of claim 1, wherein the composition further comprises a carrier solvent.

11. The method of claim 10, wherein the carrier solvent is selected from the group consisting of lipophilic organic diluents, alcohols, ethylene glycol, propylene glycol, dipropylene glycol, ether, chloroform, benzene, carbon disulfide, oils including non-volatile and volatile liquids and oils, water, and combinations thereof.

12. The method of claim 11, wherein the alcohol is selected from the group consisting of ethanol, propanol, isopropanol, butanol, pentanol, hexanol, heptanol, octanol, phenyl ethyl alcohol, and combinations thereof.

13. The method of claim 1, wherein the composition further comprises an additional component selected from the group consisting of a surfactant, a thickener, a foaming agent, a lubricant, a propellant, a fragrance, and combinations thereof.

14. The method of claim 1, wherein the composition is formulated as a spray composition.

15. The method of claim 14, wherein the spray composition comprises about 0.0003% to about 0.0005% (w/w) androstenone, about 0.0003% to about 0.0005% (w/w) androstenol (w/w), about 0.0003% to about 0.0005% (w/w) quinoline, about 3% to about 7% (w/w) isopropanol, and about 89% to about 93% (w/w) water.

16. The method of claim 14, wherein the spray composition comprises about 0.001% to about 0.003% (w/w) androstenone, about 0.001% to about 0.003% (w/w) androstenol, about 0.001% to about 0.003% (w/w) quinoline, about 3% to about 7% (w/w) isopropanol, and about 89% to about 93% (w/w) water.

17. The method of claim 1, wherein the composition is formulated as a foaming composition.

18. The method of claim 17, wherein the foaming composition comprises about 0.001% to about 0.003% (w/w) androstenone, about 0.001% to about 0.003% (w/w) androstenol, about 0.001% to about 0.003% (w/w) quinoline, about 1% to about 10% (w/w) glycerin lubricant, about 70% to about 95% (w/w) water, and about 5% to about 20% (w/w) propellent.

19. The method of claim 1, wherein the composition is administered to the suid's olfactory system.

20. The method of claim 1, wherein administering the pheromone composition comprises spraying the suid with the composition, placing the composition in the environment of the suid, or spraying the suid's environment with the composition.

21. The method of claim 20, wherein administering the pheromone composition comprises placing the composition in the environment of the suid.

22. The method of claim 21, wherein placing the composition in the environment of the suid comprises applying the composition to a rope in the environment of the suid.

23. The method of claim 1, wherein the pheromone composition is administered for a duration of time ranging from about 10 to about 50 days.

24. The method of claim 23, wherein administering the pheromone composition comprises placing the composition in the environment of the suid at a rate of about 3 to about 5 ml daily for a period of time ranging from about 25 to about 35 days.

25. The method of claim 1, wherein the method further comprises administering the pheromone composition to the peri-pubertal suid after onset of estrus in the peri-pubertal suid.

26. The method of claim 1, wherein the method further comprises administering the pheromone composition to the peri-pubertal suid to induce onset of estrus and continue administration of the composition after onset of estrus in the peri-pubertal suid.

27. The method of claim 1, wherein the method further improves performance of the peri-pubertal suid.

28. A method of improving performance of a peri-pubertal suid comprising: administering a pheromone composition to the suid, the composition comprising a combination of pheromonal agents, wherein the pheromonal agents comprise at least one steroid hormone and quinoline; wherein improving performance of a peri-pubertal suid comprises stimulating early onset of estrus in the peri-buertal suid, stimulating reproductive behavior, synchronizing estrus in the peri-pubertal suid, stimulating weight gain and final weight at market or breeding, increasing feeding behavior, increasing average daily gain, increasing playing behavior, increasing development of ovaries and reproductive tract, and combinations thereof.

* * * * *